United States Patent [19]
Cook et al.

[11] 3,933,852

[45] Jan. 20, 1976

[54] PROCESS FOR MAKING N-METHYL NITROPHTHALIMIDES

[75] Inventors: Newell C. Cook, Schenectady; Gary C. Davis, Albany, both of N.Y.

[73] Assignee: General Electric Company, Schenectady, N.Y.

[22] Filed: May 8, 1974

[21] Appl. No.: 468,012

[52] U.S. Cl............. 260/326 N; 260/520; 260/546; 260/47 CP
[51] Int. Cl.² ................................... C07D 209/34
[58] Field of Search ............................ 260/326 N

[56] References Cited
OTHER PUBLICATIONS

Tech. of Chem. Vol. 2, (1973) pp. 770–771.
Academic Des. Sciences, Vol. 242, (1956) pp. 916–918.
Chem. Abst., Vol. 77, (1972) 19327y, 19330u, 19331v.
Org. Syntheses Collective, Vol. I, (1941) pp. 408–409.

Primary Examiner—Lewis Gotts
Assistant Examiner—D. R. Phillips
Attorney, Agent, or Firm—Joseph T. Cohen; Jerome C. Squillaro

[57] ABSTRACT

Nitrated derivatives of N-methylphthalimide can be obtained by contacting N-methylphthalimide dissolved in concentrated sulfuric acid with concentrated nitric acid at a temperature from about 60°–80°C., and thereafter extracting the formed nitro derivatives with methylene chloride.

7 Claims, No Drawings

PROCESS FOR MAKING N-METHYL NITROPHTHALIMIDES

This invention is concerned with a process for making nitrated derivatives of N-methylphthalimide. More particularly, the invention is concerned with a process for making nitro N-methylphthalimides of the formula

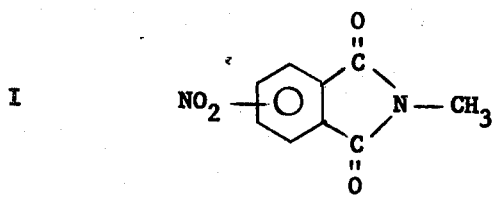

I which comprises forming a solution of N-methylphthalimide in a solvent composed of at least 98%, e.g., 98 to 103% sulfuric acid, contacting the said solution with 98 to 100% nitric acid within a temperature range of from 60° to 80°C., and extracting the nitrated products with methylene chloride to obtain the desired nitro derivatives of N-methylphthalimide.

N-methyl-3-nitrophthalimide and N-methyl-4-nitrophthalimide are employed in the preparation of polymers having good heat resistance. More particularly, these nitrophthalimides are first reacted with the dialkali-metal salt of bisphenol-A [(2,2-bis-4-hydroxyphenyl)propane] to form a derivative having the formula

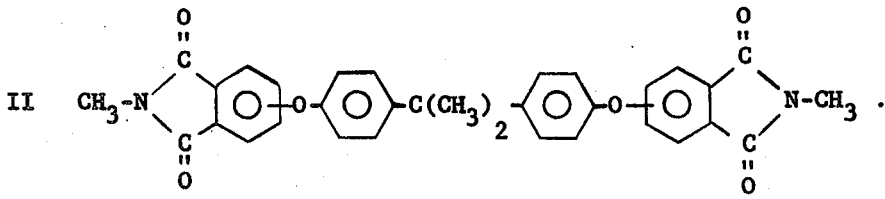

II

Thereafter the bisimide of formula II can be treated with aqueous sodium hydroxide and water to form the corresponding tetracarboxylic acid having the formula

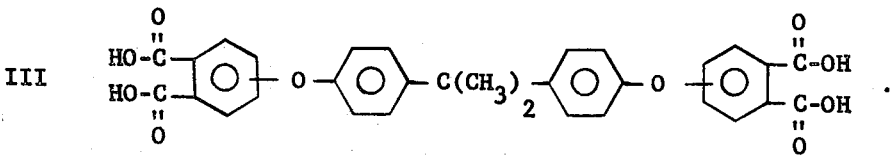

III

By suitable treatment of the tetra-acid with, for instance, glacial acetic acid and acetic anhydride, one can obtain the corresponding dianhydride, for instance, 2,2-bis[4-(3,4-dicarboxyphenoxy)phenyl]propane dianhydride. These dianhydrides can then be reacted with organic diamines for example, 4,4'-diaminodiphenylmethane, m-phenylene diamine, 4,4'-diaminodiphenyloxide, etc., to give polymers having extremely good high-temperature properties. Polyetherimide polymers derived in the above manner are more particularly disclosed and claimed in the copending application of Darrell R. Heath and Joseph G. Wirth in Ser. No. 319,327, filed Dec. 29, 1972 (now U.S. Pat. No. 3,847,867 issued Nov. 12, 1974), which in turn is a continuation-in-part of application Ser. No. 108,151 of the same applicants filed Jan. 20, 1971 (now U.S. Pat. No. 3,787,475 issued Jan. 22, 1974), both applications being assigned to the same assignee as the present invention. The polyetherimides obtained in the manner described above can be used in various molding applications, for instance, as housings for appliances and for motors, as brake linings where heat resistance and other improved physical properties are essential, etc.

The nitration of many organic compounds has in the past used processes which are more amenable for batch operation than continuous processing. Because of the limitation of batch operation and the extreme acidic conditions employed, the yields of the desired product have not been as good as desired, and some times the reactants and some of the other materials used in the process have either been degraded or in some other way have usually been rendered unfit for reuse or recycle. If attempts are made to reuse or recycle the reactants or other materials used in the process, the expense of such activity has been sufficiently high as to usually discourage such use or recycle.

Unexpectedly, we have discovered that we are able to nitrate aromatic compounds such as N-methylphthalimide by a simple process and to isolate the desired nitrated products in almost quantitative yields. Also, our process permits reuse and recycle of the unused reactants, the sulfuric acid solvent, and the $CH_2Cl_2$ employed for extraction purposes. More particularly, we have discovered that we can nitrate N-methylphthalimide to give the 3-isomer and the 4-isomer in close to quantitative yields by using a concentrated sulfuric acid as solvent for the reaction, employing concentrated nitric acid as the nitrating agent, and extracting the formed products with methylene chloride. In accordance with our discovery, the reaction is carried out expeditiously and at moderate temperatures of about 60° to 80°C., and the sulfuric acid and the methylene chloride used can be recycled and employed for additional reaction in essentially unchanged form subject only to removal of about 5 to 7% of the water now present in the sulfuric acid solvent as a result of having been diluted by the water of reaction formed during the nitration process. Finally, in contrast to the usual batch processing employed for nitration reaction, our process is especially amenable to a continuous nitration reaction wherein the nitric acid is fed in simultaneously with the sulfuric acid solution of the N-methylphthalimide, and the effluent is readily treated with the methylene chloride to extract the nitrated N-methylphthalimide; the unused reactants and other materials used can then be recycled either as obtained or with slight modification, specifically in the removal of about 5 to 7% water in the sulfuric acid solvent resulting from the nitration reaction.

There are several critical features of our invention. In the first place, the nitration reaction should be carried out at a temperature of between 60° to 80°C., preferably from 65° to 75°C. If the reaction is carried out above 80°C. yields are usually decreased due to reactions, such as increased oxidation and hydrolysis. If the reaction is carried out below 60°C., the reaction rate is appreciably decreased and, thus, economically unattractive.

The use of the methylene chloride as the extractant for isolating the formed nitro derivatives is also critical for a number of unexpected reasons. Attempts to employ other halogenated derivatives such as chloroform, carbon tetrachloride, and methyl chloroform were unsuccessful for various reasons, including tendencies of the halogenated compositions to degrade or be converted to other products, or else did not have the desired volatility and solubility affinity for the nitrated product to insure efficient and rapid utilization of the extractant. Only methylene chloride was found able to avoid the above problems and the only lower aliphatic halide tried which was able to maintain its integrity sufficiently in the strongly acidic environment. The rate of use of the methylene chloride can be varied widely and is not critical. Thus, for each liter comprising the nitrated product and sulfuric acid solvent, one can advantageously employ from about 0.5 to 8 to 10 liters or more methylene chloride, depending on the technique used in the extraction. Maximum contact of the methylene chloride with the sulfuric acid solution should be maintained in order to promote efficient extraction of the nitrated N-methylphthalimide.

The sulfuric acid solvent initially employed must be within 98–103% $H_2SO_4$. If lower concentrations of sulfuric acid solvent are employed initially, there is greater attack on the methyl group due to hydrolysis followed by oxidation, and the amount of water liberated from the nitration reaction and oxidation will dilute the sulfuric acid below 92–93% sulfuric acid concentration; this in turn will cause precipitation of the nitrated N-methylphthalimide, thereby causing serious separation problems during extraction. If the concentration of the resultant sulfuric acid (after the nitration reaction has taken place) is in excess of about 95% sulfuric acid, then the nitrated product is so bound to the sulfuric acid that the nitrated product can not be efficiently extracted initially with the $CH_2Cl_2$. It may be necessary to add a little water to the reaction mixture to adjust the sulfuric acid concentration to from about 92 to 95%.

The amount of sulfuric acid used can range, on a weight basis, from 2 to 4 parts sulfuric acid per part N-methylphthalimide. The lower ratios of acid to the imide are convenient when higher strength $H_2SO_4$ (i.e., greater than 100%) is used, and the higher ratios are beneficial when lower strength $H_2SO_4$ (less than 100%) is employed.

Also the concentration of the nitric acid must be again within 98 to 100% concentration in order to minimize the amount of water added so as not to unduly dilute the sulfuric acid. The amount of nitric acid used should be relatively close to the stoichiometric amount required to attach one $NO_2$ group on the aromatic nucleus of the N-methylphthalimide; otherwise, any substantial excess of the nitric acid will cause oxidation of the nitrophthalimide. Slight excess of nitric acid, e.g., from 1.1 to 1.3 mols nitric acid per mol N-methylphthalimide should be used in order to compensate for the nitric acid lost in oxidative side reactions.

In carrying out the reaction, the N-methylphthalimide and the concentrated sulfuric acid solvent are mixed together in a reactor equipped with a stirrer and means for heating or cooling the reactor. After heating the solution to the desired temperature and while stirring is maintained, the concentrated nitric acid is added slowly, under the surface of the sulfuric acid solution, over a period of time advantageously ranging from about 10 minutes to about one hour or more. After stirring the mixture of the sulfuric acid solution and the nitric acid for a period of time ranging from about 30 minutes to about 2 to 3 hours at about 60° to 80°C., the reaction mixture is led to a closed loop extractor for the continuous extraction of the sulfuric acid solution with the $CH_2Cl_2$. This closed loop extractor can resemble a Dean-Stark apparatus and consists of an extraction column equipped with a stirrer into which the reaction product is introduced. Methylene chloride (extractant) is introduced continuously into the bottom of the extraction column. At the upper end of the extraction column is an arm through which the overflow of the extractant and reaction product (separated from the $H_2SO_4$) is carried into a reservoir equipped with a heater operable within a range of from about room temperature to 100°C. whose function is to evaporate the $CH_2Cl_2$ and concentrate the nitrated N-methylphthalimides. The $CH_2Cl_2$ vapor is condensed and recycled by gravity to the bottom of the extraction column and continues recycling until extraction is complete. At this point, all the nitrated product is in the $CH_2Cl_2$ contained in the reservoir.

In order that those skilled in the art may better understand how the present invention may be practiced, the following example is given by way of illustration and not by way of limitation.

EXAMPLE 1

About 161 grams (1 mol) N-methylphthalimide was added to 353 grams of 100% $H_2SO_4$ in the aforementioned reactor. The solution was heated with stirring to 70°C. and thereafter 76.8 grams (1.2 mols) 98.1% $HNO_3$ was added slowly over a period of 20 to 25 minutes with the addition being carried out under the surface of the solution. Stirring of the reaction mixture was continued for an additional hour at 70°C. and thereafter, the solution was cooled to room temperature. The resulting reaction solution was then transferred to the closed loop extractor described above for the continuous extraction of the acid solution. About 1 liter of methylene chloride was added to the extraction apparatus at the time the extraction was commenced. The amount of methylene chloride continually passing through the sulfuric acid reaction product was at the rate of about 3 liters per hour. The first continuous extraction was carried out for about 3½ hours and drained of the first extract solution; then another liter of methylene chloride was added to the reservoir and a second extraction was commenced and allowed to run for about 5 hours. The speed of the second extraction can be accelerated by adjusting the concentration of the sulfuric acid to as low as 90%, thus advantageously operating the extraction step in a range of about a 90–95% concentration of the sulfuric acid. Both extractions, which consisted mainly of the nitrated N- methylphthalimides, were passed through a column of silica gel to remove residual acid, for example, sulfuric acid or nitric acid, in an amount equal to approximately 3%, and then the mixture was evaporated under vacuum in a rotary film evaporator. As a result of these steps, it was found that the yield was as follows:

A. First extraction 161.8 grams (87.9% of extracted material)
B. Second extraction 22.2 grams; Total 184.0 grams This constituted a yield of 89.3% of the desired nitrated N-methylphthalimides. A gas chromotographic analysis showed the product to consist of about 94% 4-nitro-N-methylphthalimide, about 5% 3-nitro-N-methylphthalimide, and about 1% of unreacted N-methylphthalimide.

By extracting the nitration product from the sulfuric acid with $CH_2Cl_2$ excessive dilution of the acid can be avoided. This makes it possible to economically remove by distillation the water formed in the nitration and thus reconcentrate the $H_2SO_4$ to a strength sufficient for reuse in nitration. To eliminate color and the accumulation of organic material (resulting from oxidation) in the sulfuric acid, $NO_2$ is bubbled into the sulfuric acid while evaporating water at 250° to 325°C. This oxidizes the organic material to $CO_2$ and $H_2O$ which are eliminated and makes it possible to recover colorless or near colorless 98.3% $H_2SO_4$, the constant boiling composition. Addition of $SO_3$ to the constant boiling acid can readily convert it to 100% concentration, or higher strength if desired.

The following example illustrates this technique:

1000 grams $H_2SO_4$, (dark red color) resulting from following the above nitration procedure, was placed in a 1000 ml three-neck flask. The acid was heated to 260°C., at which point 20 ml $H_2O$ was removed and collected. About 15 grams of $NO_2$ was bubbled into the acid as the temperature rose to 320° in the pot and 323°C. for the distillate over a period of 90 minutes. Just before the end of the 15 grams $NO_2$ addition, the sulfuric acid became almost colorless. The sulfuric acid remaining in the reaction vessel had a density of 1.84, indicating essentially pure 98.3% $H_2SO_4$.

It will of course be apparent to those skilled in the art that in addition to the temperatures and concentrations employed in the foregoing example, other temperatures of reactions and concentrations of ingredients can be used within the limits prescribed above without departing from the scope of the invention.

What we claim as new and desire to secure by Letters Patent of the United States is:

1. In the process for isolating a mixture of N-methyl-3-nitrophthalimide and N-methyl-4-nitrophthalimide from a solution of the latter in concentrated sulfuric acid, the improvement which comprises extracting the aforesaid two nitrophthalimides with methylene chloride as the extractant.

2. The process for obtaining nitrated derivatives of N-methylphthalimide which comprises forming a solution of N-methylphthalimide in a solvent composed of 98–103% concentrated sulfuric acid, contacting the said solution with a 98–100% concentrated nitric acid within a temperature range of 60° to 80°C. and thereafter extracting the nitrated products with methylene chloride to obtain a mixture composed essentially of N-methyl-3-nitrophthalimide and N-methyl-4-nitrophthalimide.

3. The process as in claim 2 wherein the nitric acid is present in essentially a molar equivalent per mol of the N-methylphthalimide.

4. The process as in claim 2 wherein the temperature is in the range of from 65° to 75°C.

5. The process as in claim 2 where the treatment of the sulfuric acid solution of the N-methylphthalimide with the nitric acid and the subsequent extraction of the formed nitro derivatives with the methylene chloride is carried out on a continuous basis.

6. The process as in claim 2 wherein the sulfuric acid concentration being extracted by the methylene chloride is maintained within the range of 90 to 95%.

7. The process as in claim 5 wherein the sulfuric acid derived from the nitration reaction is freed of organic materials and decolorized by treatment with $NO_2$ at elevated temperatures.

* * * * *